United States Patent
Radatus et al.

(10) Patent No.: US 6,635,753 B1
(45) Date of Patent: *Oct. 21, 2003

(54) PROCESS FOR THE PREPARATION OF SUBSTANTIALLY PURE STAVUDINE AND RELATED INTERMEDIATES USEFUL IN THE PREPARATION THEREOF

(75) Inventors: Bruno K. Radatus, Brantford (CA); K. S. Keshava Murthy, Brantford (CA)

(73) Assignee: Brantford Chemicals Inc., Brantford (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/163,321

(22) Filed: Sep. 30, 1998

(51) Int. Cl.[7] .............................. C07H 19/073
(52) U.S. Cl. ................. 536/28.54; 536/28.1; 536/28.2; 536/28.4; 536/28.52
(58) Field of Search .............................. 536/28.2, 28.1, 536/28.52, 28.54, 28.4

(56) References Cited

U.S. PATENT DOCUMENTS

| | | |
|---|---|---|
| 4,904,770 A | 2/1990 | Starrett, Jr. et al. ........... 536/23 |
| 5,539,099 A | 7/1996 | Skonezny et al. ......... 536/28.2 |

FOREIGN PATENT DOCUMENTS

EP 6535435 * 5/1995

OTHER PUBLICATIONS

Eaton et al., J. Chem. Soc., Faraday Trans. 1, vol. 84 (10), 1988, pp. 3459–3473.*

Horwitz, J.P. et al., "Nucleosides IX. The Formation of 2',3'–Unsaturated Pyrimidine Nucleosides via a Novel β–Elimination Reaction", *J. Org. Chem.*, (1996) 31, 205.

Mansuri, M.M. et al., "1–(2, 3–Dideoxy–β–D–*glycero*–pent–2–enofuranosyl)thymine. A Highly Potent and Selective Anti–HIV Agent", *J. Med. Chem.*, (1989) 32, 461.

Adachi, T. et al., "Synthesis of Uracil and Thymine Nucleosides of Unsaturated 5–Aminoacyl)Aminopentofuranoses", *Carbohydrate Research*, (1979) 113.

Cosford, Nicholas D.P. et al., "Selenium Nucleophiles for the Preparation of Antiviral Nucleosides", *J. Org. Chem.*(1991) 2161.

* cited by examiner

*Primary Examiner*—James O. Wilson
*Assistant Examiner*—Howard V Owens, Jr.
(74) *Attorney, Agent, or Firm*—Marcelo K. Sarkis; Ivor M. Hughes; Neil Hughes

(57) ABSTRACT

There are disclosed novel Stavudine solvates as follows: Stavudine NN-dimethyllacetamide solvates; Stavudine NN-dimethylacrylamide solvates and Stavudine NN-dimethylpropionamide solvates and processes for producing Stavudine NN-dimethylacetamide solvates, Stavudine NN dimethylacrylamide solvates and Stavudine NN dimethylpropionamide solvates which results in pure Stavudine.

31 Claims, No Drawings

PROCESS FOR THE PREPARATION OF SUBSTANTIALLY PURE STAVUDINE AND RELATED INTERMEDIATES USEFUL IN THE PREPARATION THEREOF

BACKGROUND OF THE INVENTION

The synthesis of Stavudine was first reported by J. P. Horwitz et al (J. Org. Chem. (1996) 31, 205) starting from 3',5'-dimesylthymidine as shown in Scheme 1.

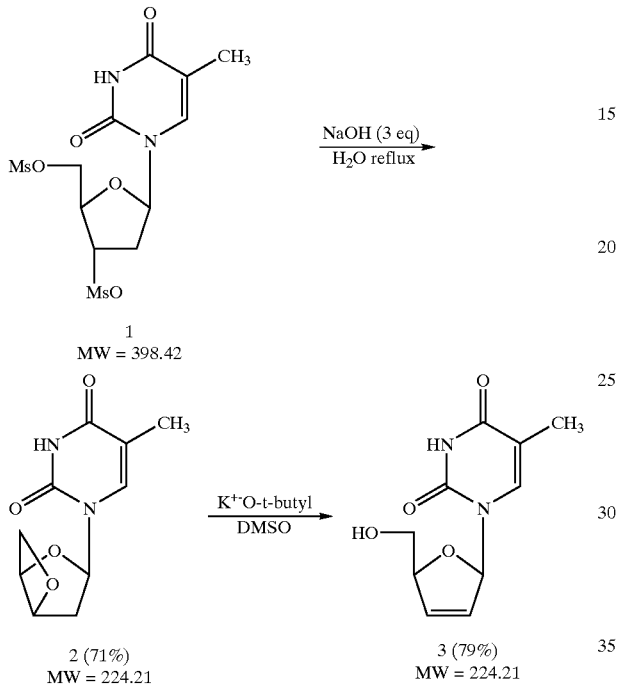

In this synthesis, dimesylthymidine 1 was first treated with sodium hydroxide (3 equivalents) in refluxing water for 2 hours and after work-up the resultant 3,5-anhydrothymidine was treated with potassium t-butoxide in dimethylsulfoxide (DMSO) at room temperature for 2 hours. The reaction mixture was neutralized, evaporated to dryness and after a series of manipulations which included extraction, decolourization, precipitation and recrystallization, gave Stavudine in 79% yield and an overall yield of 56%.

The above procedure was modified by Mansuri et al (J. Med. Chem. (1989) 32, 461) where the potassium t-butoxide/DMSO mixture was poured into 30 volumes of toluene whereby the Stavudine precipitates as the potassium salt along with excess potassium t-butoxide. This modification avoided the distillation of DMSO which caused decomposition of Stavudine. The salt was neutralized in water and the product precipitated. The precipitate was extracted with acetone and then evaporated to dryness to give an off-white solid in 57% yield.

A similar procedure was disclosed by Starret, Jr. et al (U.S. Pat. No. 4,904,770 to Bristol), Mr. Starret was also an author of the Mansuri publication.

A major problem with the above procedure is that the Stavudine potassium salt is sensitive to both moisture and excessive drying thus, resulting in impurities.

Adachi et al. (Carbohydrate Research (1979) 113) overcame some of the decomposition. problems by employing sodium hydroxide in hexamethylphosphorictriamide (HMPA). The HMPA was removed by forming a chloroform complex in an aqueous mixture and Stavudine was isolated from the aqueous phase.

Stavudine has also been proposed to be produced from 5-methyluridine in U.S. Pat. No. 4,904,770 via three proposed routes and from 3'-phenylsilinyl-5'-tritylthymidine (Cosford et al, J. Org. Chem. (1991) 2161) with the latter process requiring column chromatography for purification.

P. M. Skonezny et al. (U.S. Pat. No. 5,539,099 to Bristol) purports to have developed the route for producing Stavudine as shown in Scheme 2.

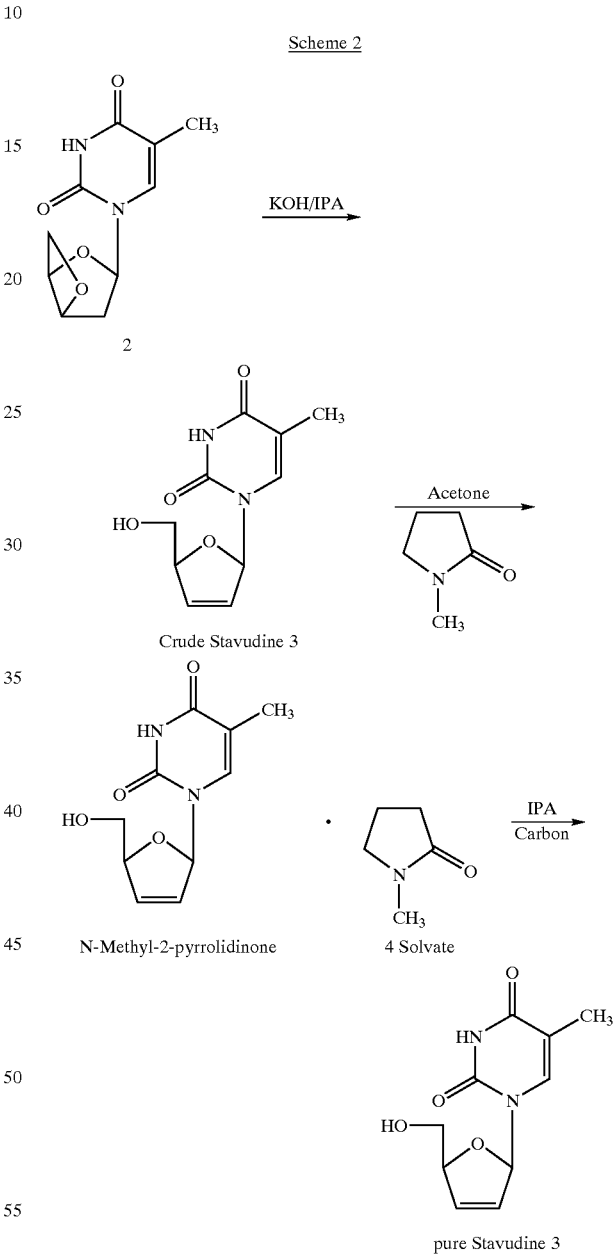

However, all of the above discussed processes have one major drawback in common in that the final purity of Stavudine was less than the desired 99.5%, at least. Known and difficult to remove impurities using conventional techniques were still present, some of which were thymine, thymidine, threo-thymidine, 3,5-anhydrothymidine and 5'-O-[stavudin-5'''-yl]-threo-thymidine with the latter (Scheme 3) being particularly difficult to remove.

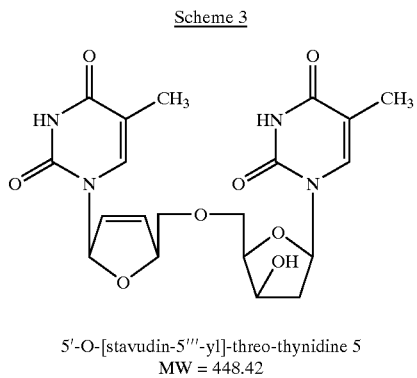

Scheme 3

5'-O-[stavudin-5'''-yl]-threo-thynidine 5
MW = 448.42

Further, U.S. Pat. No. 5,539,099 teaches the use of only N-methyl-2-pyrrolidinone as suitable to form a solvate of Stavudine whose recovery requires the use of an aprotic ester, amide or ketone solvent. No consideration is given for their use to form a solvate.

It is therefore an object of this invention to provide an improved process which is more efficient, using less toxic materials (for example, using solvents which are at least 20% less toxic than N-Methyl-2-pyrrolidinone) and providing a cleaner and purer product before recrystallization steps are carried out.

Further and other objects of the invention will be realized by those skilled in the art from the following summary of invention and detailed description thereof.

SUMMARY OF THE INVENTION

The present invention provides an improved process for producing substantially pure Stavudine on a large or commercial scale. The invention further provides a process for manufacturing substantially pure Stavudine where the above mentioned impurities found in the prior art processes and other impurities are present at levels substantially much lower than the prior art processes or are not detected at all.

Therefore, according to one aspect of the invention, we provide process for preparing substantially pure Stavudine by preparing a solvate of Stavudine for example, a Stavudine amide by reacting Stavudine with at least one compound selected from the group consisting of N,N-dimethylacetamide, N,N-dimethylacrylamide and N,N-dimethylpropionamide, (preferably Stavudine with N,N-dimethylacetamide) and thereafter, recovering substantially pure Stavudine by breaking the solvate produced.

According to another aspect of the invention, we provide a process for preparing a solvate of Stavudine by reacting Stavudine (for example, crude Stavudine with at least one compound selected from the group consisting of N,N-dimethylacetamide, N,N-dimethylacrylamide and N,N-dimethylpropionamide, (preferably Stavudine with N,N-dimethylacetamide).

According to another aspect of the invention, we provide a process for producing at least one of the following novel compounds selected from the group consisting of Stavudine .N,N-Dimethylacetamide (DMA) solvate, Stavudine .N,N-Dimethylacrylamide (DMAC) solvate, and Stavudine .N,N-Dimethylpropionamide (DMP) solvate, all of which are new compounds and which precipitate as substantially white crystals from N,N-dimethylacetamide, N,N-dimethylacrylamide and N,N-dimethylpropionamide respectively.

According to another aspect of the invention, we further provide a process for the manufacture of Stavudine which leaves most of the impurities behind in the mother liquors.

According to another aspect of the invention, we further provide a process for the breaking of a Stavudine solvate preferably Stavudine DMA solvate by dissolving said solvate in at least one suitable solvent preferably but, not limited to, water, acetone and isopropanol, or combinations thereof, and then concentrating, preferably so that about 1 to 5 volumes of solvent remains depending on the solvent choice, whereupon substantially pure white Stavudine is precipitated if desired. Thereafter, the substantially pure Stavudine is filtered, washed and dried.

Thus, according to another aspect of the invention, Stavudine has been provided in a purity of at least 99.5%. This Stavudine may be combined with suitable adjuvants, carriers, or diluents to prepare dosage forms of pharmaceutical compositions containing Stavudine (such as tablets, capsules, injectibles) in all manner known to persons skilled in the art.

Embodiments of the present invention will now be illustrated.

DISCUSSION OF EMBODIMENTS OF THE INVENTION

In another embodiment, there is provided a process for production of substantially pure Stavudine comprising:

a) the dissolution of crude Stavudine in preferably 1 to 2 parts of a solvent, preferably N,N-dimethylacetamide (DMA), more preferably 1.5 parts of N,N-dimethylacetamide (DMA) at elevated temperatures. If insoluble solids are present after dissolution the mixture can be filtered. To aid in the filtration, the mixture can be diluted with aprotic or protic solvents such as acetone, ethyl acetate, methanol, ethanol or isopropanol and later removed by distillation;

b) the solution from (a) is cooled to ambient temperature or lower whereupon a precipitate forms. If the solution was diluted with a low boiling solvent then that solvent is first removed by distillation before cooling to give crystalline Stavudine DMA solvate;

c) the precipitate is filtered and washed with an aprotic solvent such as acetone, ethyl acetate, methylisobutyl ketone and the like to give substantially white crystals in substantially high yield which have the composition of Stavudine .N,N-dimethylacetamide solvate as indicated by $^1$H NMR spectroscopy (see examples following);

d) the above procedure can be repeated with N,N-dimethylacrylamide and N,N-dimethylpropionamide to give the corresponding Stavudine solvate.

In one embodiment, the invention also provides a compound selected from the group of compounds consisting of:

a) Stavudine N,N-dimethylacetamide solvate;
b) Stavudine N,N-dimethylacrylamide solvate; and
c) Stavudine N,N-dimethylpropionamide solvate.

In another embodiment, the invention further provides a process for making Stavudine comprising breaking the solvate of a compound selected from the group of compounds consisting of:

a) Stavudine N,N-dimethylacetamide solvate;
b) Stavudine N,N-dimethylacrylamide solvate; and
c) Stavudine N,N-dimethylpropionamide solvate, Preferably, the solvates are broken down by dissolving them in polar protic or aprotic solvents or combinations thereof at elevated temperatures between about 50–100° C. concentrating, if necessary, and then cooling to cause precipitation.

Preferably, the solvents can be water, alcohols with 1 to 4 carbons, ketones such as acetone, methyl ethyl ketone and methyl isobutyl ketone, and amides other than those which form the solvates themselves.

According to another embodiment, the invention further provides a process for making at least one of the compounds selected from the group of compounds consisting of:

a) Stavudine N,N-dimethylacetamide solvate;
b) Stavudine N,N-dimethylacrylamide solvate; and
c) Stavudine N,N-dimethylpropionamide solvate, which comprises reacting Stavudine with a compound selected from the group consisting of N,N-dimethylacetamide, N,N-dimethylacrylamide and N,N-dimethylpropionamide, dissolving the solvate in polar solvents such as water, acetone, isopropanol or a combination thereof at an elevated temperature; thereafter, concentrating the solution to a small volume where preferably 1 to 5 volumes of solvent remains depending on the solvent choice for example; where water is the solvent, the volume of water can be about 1.39 times relative to the Stavudine content; where acetone is the solvent, the volume of the solvent remaining can be about 5 times where isopropanol is the solvent, the volume can be about 3 times, and thereafter, filtering the resulting crystals, washing with a polar solvent preferably acetone or isopropanol and drying to give substantially pure white crystalline Stavudine in substantially high yield.

The % purity of the product obtained by this process generally exceeds 99.5% and in some instances exceeds 99.7%.

Several advantages in carrying out embodiments of the invention include but are not limited to the following:

When the crystallization solvent is essentially DMA, the impurity levels are very low which is especially important for thymine and stavudinyl-threo-thymidine impurities since they are particularly difficult to remove using conventional techniques.

An anti-solvent such as acetone or ethyl acetate is not required except for handling purposes only. When an anti-solvent was employed during crystallization, the resulting solvate had more colour and more impurities present, especially thymine and Stavudinyl-threo-thymidine and in particular the latter. Therefore, when N,N-dimethylacetamide was essentially the only solvent present, the resultant solvate was substantially white and impurity levels were substantially very low, a very important consideration considering difficulties in removing the two above mentioned impurities, thymine and Stavudinyl-threo-thymidine.

Since the solvate is usually substantially white, it is not necessary to employ charcoal during the final isolation stage.

N,N-dimethylacetamide is a more common, more readily available, less hazardous, less toxic and less expensive solvent than N-Methyl-2-pyrrolidinone found in the prior art.

The following examples are provided as illustrative of the invention.

EXAMPLE 1

1. Purified Stavudine-N,N-Dimethylacetamide Solvate from Crude Stavudine

Method A

Crude slightly beige Stavudine (15.9 g, 92.03% pure, 0.0653 mole) was combined with N,N-dimethylacetamide (23.86 g, 1.5 parts) and heated to 75–80° C. when all solids had dissolved. Heating was stopped and the solution was allowed to cool on its own and within minutes crystals began to form. The mixture was further cooled to 0–50° C. and maintained for 2.5 hours. The crystals were filtered, washed with acetone (2×8 mL) and dried to give white Stavudine-DMA solvate (16.04 g, 0.0515 mole, 78.9%) with a chromatographic purity of 99.59%. Since a filtration step was not employed above, when isolating pure stavudine a filtration step would have to be introduced. A further purified Stavudine.DMA solvate had an HPLC purity of 99.98% and the following characterization. The melting point was 132.4–134.8° C. The optical rotation $[\alpha]_D^{25}$=−31.2°. Analyzed for $C_{14}H_{21}N_3O_5$ (MW=311.33): C;54.01; H,6.80; N;13:50 Found: C, 53.96; H,6.76; N,13.35. The 300 MHz $^1$HNMR in DMSO-d6 showed. δ1.74 (s, 3H, Stavudine-$CH_3$); 1.97 (s,3H, $CH_3$); 2.80 and 2.95 (2×s, 2×3H, $N(CH_3)_2$); 3.61 (m,2H, 2×H-5'); 4.78 (s, 1H,H-4'); 6.80 (t, 1H, 2×J=1.4, H-2'); 7.66 (s, 1H, H-6); 11.30 (s, 1H, NH). The Stavudine portion of the above spectrum agrees with the literature values (J. Med, Chem, 32, 461 (1989))

The mother liquors from the solvate formation could be further processed by a combination of fractional crystallization and column chromatography to yield the difficult to remove impurity 5'-O-(stavudin-5'''-yl)-threo-thymidine.

The Stavudinyl-threo-thymidine had a chromatographic purity of 99.51% (Thymine=0.08%, Stavudine=0.04%, impurity at 48.7min=0.21%) and its characterization is as follows. The melting range was 193–195° C. The optical rotation $[\alpha]_D^{25}$ =−30.5 (cl, DMSO). Analyzed for $C_{20}H_{24}N_4O_8$ (MW=448.42): C,53.57; H, 5.39, N, 12.49. Found: C,53.48; H,5.31; N.12.39. The 300 MHz $^1$HNMR spectrum in DMSOd6 showed: δ1.72 and 1.77 (2× s, 6H, 2×$CH_3$); 1.84 (dd, 1H, J=14.7, 2.2, H-2') 2.5 (dd, 1H, J=8.3, H-2'); 3.7(m, 4H, 2×H-5' and 2×H-5'''), 3.94(m, 1H, H4'); 4.26 (s, 1H, H-3'); 4.9 (s, 1H, A4'''), 5.4 (s, 1H, OH); 5.92 (d, 1H, J 0 5.6, H-2'''); 6.10 (dd, 1H, H-1'); 6.42 (d, 1H, J=5.9, H-2''), 6.83 (m, 1H, H-3'''), 7.41 and 7.79 (2×s, 2H, H-6 and H-6'), 11.29 (s,2H, 2×NH). The above two nucleoside moieties were differentiated with the help of an NMR COSEY experiment. The threo-configuration for the $C_3^1$—OH was assigned on the basis of how Stavudine and the oxetane would come together to form this impurity.

The 75 MHz $^{13}$C NMR spectrum in DMSO-d6 showed: δ13.63 and 14.18 (2×$CH_3$), 42.17 (C-2') 70.90 (C-3'), 72.02 and 73.47 (C-5' and C-5''') 84.37 (C4'), 85.22 (C-1'), 87.06 (C4'''), 90.55 (C-3''') 110.55 and 111.13 (C-5 and C-5''), 127.78 (C-1''''), 152.24 and 152.45(C-4 and C4''), 165.49 (C-2 and C-2''). The above carbons were assigned partly on the basis of a correlation between the $^1$H and $^{13}$C NMR spectra.

In a similar manner the Stavudine solvates of N,N-dimethylacrylamide and N,N-dimethylpropionamide were prepared from 6 g samples of crude Stavudine to give 7.29 g (84.3%) and 6.18 g (71.0%) respectively. The 300 MHz $^1$H NMR spectra of the solid in DMSO-d6 clearly showed one equivalent of amide for each equivalent of Stavudine.

Method B

Crude slightly beige Stavudine (17.25 g, 96.02% pure, 0.0739 mole) was combined with N,N-dimethylacetamide (25.91 g, 1.5 parts) and isopropanol (52 mL, 3 volumes) and heated to 79° C. when all solids dissolved. The cloudy mixture was filtered through dicalite and washed with isopropanol (12.5 mL). The filtrate was initially concentrated at atmospheric pressure and then a slight vacuum was applied so that the distillation occurred at 60–70° C. It was estimated that about 1.7 g of isopropanol remained. The solution was cooled, filtered, washed and dried to give 17.30 g of Stavudine-DMA solvate (0.0556 mol, 75.2%) with a chromatographic purity of 99.59%.

Method C

Crude white Stavudine (12.10 g, 94.25% pure, 0.0509 mole) was combined with DMA (18.15 g, 1.5 parts) and acetone (36 mL) and heated to 56° C. when all solids had dissolved. The cloudy mixture was filtered, distilled to remove acetone, cooled, filtered, washed with acetone and dried to give 12.35 g of white Stavudine-DMA solvate (0.0397 mole, 78.1%) with a chromatographic purity of 99.35%.

The following Table 1 summarizes the improvements in chromatographic purity for the above examples.

The Stavudine-DMA solvate (15.2 g, 0.0488 mole) was combined with water (2.74 g) and acetone (220 mL) and

TABLE 1

| | | Chromatographic Purities % | | | | |
|---|---|---|---|---|---|---|
| Method | Starting Stavudine | Stavudine | Thymine | Threothymidine | Oxetane | Stavudinyl-threothymidine |
| A | Stavudine | 92.03 | 0.36 | 0.28 | 2.79 | 3.77 |
| A | Stavudine DMA | 99.59 | 0.13 | | 0.14 | 0.09 |
| B | Stavudine | 96.02 | 0.38 | 0.23 | 0.12 | 2.32 |
| B | Stavudine DMA | 99.59 | 0.06 | | 0.01 | 0.09 |
| C | Stavudine | 94.25 | 0.53 | 0.33 | 0.31 | 3.52 |
| C | Stavudine DMA | 99.35 | 0.23 | 0.02 | 0.02 | 0.12 |

The above three methods were presented to illustrate different ways of obtaining the Stavudine DMA. Method A showed Stavudine and the solvent being combined, heated to dissolve, cooled to crystallize and then isolated. Methods B and C illustrated the use of protic and aprotic solvents such as isopropanol and acetone to aid in the filtration (prevents premature crystallization during filtration) of the solution to remove inorganic salts.

Method D

If the Stavudine DMA solvate is deemed not to have met specifications, it can be recrystallized from DMA. The Stavudine DMA solvate (11.94 g) from Method C was combined with DMA (9.47 g) and heated on a hot water bath (890° C.) to an internal temperature of 85° C. to give a clear solution. The solution was set aside with agitation to cool on its own and to crystallize. After 10 minutes, mass crystallization had occurred and it was placed on an ice-water bath. After 1.5 hours the crystals were filtered, washed with acetone (2×6 ml) and dried to give 9.41 g of Stavudine-DMA solvate (79.5%) which had a chromatographic purity of 99.99% and the impurity was thymine (0.01%). The above example illustrated how very effective recrystallization can be if it is necessary.

heated to 500° C. when only a few grains of solid remained. The hot solution was filtered to remove the remaining solid, the filtrate was distilled until about 55 mL of acetone remained. The solution was allowed to cool on its own and at about 35–40° C. it was seeded with pure Stavudine. After 70 minutes of cooling on its own it was placed on an ice-water bath for one hour. The mixture was filtered, washed with acetone (2×11 mL) and air dried to give 8.32 g (0.0371 mole, 76.0%) of pure white Stavudine. The HPLC results are given in Table 2.

Method G

The Stavudine-DMA solvate (15.22 g, 0.0489 mole), water (5.5 g) and isopropanol (150 mL) were combined and heated to about 70° C. when all solids had dissolved to give a clear colourless solution, heating was continued so as to distill the solution at atmospheric pressure until about 35 mL of isopropanol remained. The solution was allowed to cool on its own with agitation and a mass of crystals formed after 20 minutes. The mixture was 10 placed on an ice-water bath for I hour, filtered, washed with isopropanol (2×11 mL) and air dried overnight to give 10.02 g (0.0447 mole, 91.4%) of pure white crystalline Stavudine. The HPLC results are given in Table 2.

TABLE 2

| | | | | Purity (%) | | | | |
|---|---|---|---|---|---|---|---|---|
| Method | Stavudine DMA (g) | Stavudine (g) | % Yield | Stavudine | Thymine | Threo-thymidine | Oxetane | Stavudinyl-threo-thymidine |
| | Starting stavudine DMA | | | 99.70 | 0.03 | | 0.18 | 0.09 |
| E | 15.2 | 8.08 | 73.7 | 99.96 | 0.14 | | 0.12 | 0.06 |
| F | 15.2 | 8.32 | 76.0 | 99.53 | 0.12 | | 0.25 | 0.09 |
| G | 15.22 | 10.02 | 91.4 | 99.85 | 0.04 | | 0.06 | 0.05 |

Dimethylacetamide (DMA) is the preferred solvent for forming the solvate.

2. Isolation of Pure Stavudine from Stavudine-DMA Solvate

Method E

The Stavudine-DMA solvate (15.2 g, 0.0488 mole) was combined with water (15.2 g) and heated to 65° C. when all solids dissolved to give a clear colourless solution. The solution was allowed to cool on its own for an hour during which time a large amount of crystals formed. The mixture was cooled on an ice-water bath for 80 minutes, the crystals were crushed, filtered, washed with acetone and air dried to give 8.08 g (0.0360 mole, 73.7%) of pure white crystalline Stavudine. The HPLC results are given in Table 2.

Method F

The above three examples illustrate the use of three different solvent systems for breaking the solvate and isolating pure Stavudine.

The two other solvates can be similarly treated.

As many changes can be made to the embodiments without departing from the scope of the invention, it is intended that all material contained herein be illustrative of the invention and not be interpreted in a limiting sense.

The embodiments of the invention in which an exclusive property or privilege is claimed are as follows:

1. A compound as a precipitated solvate selected from the group consisting of:
  a) Stavudine N,N-dimethylacetamide solvate;
  b) Stavudine N,N-dimethylacrylamide solvate; and
  c) Stavudine N,N-dimethylpropionamide solvate.

2. The compound of claim 1 "Stavudine N,N-dimethylacetamide solvate".

3. The compound of claim 1 "Stavudine N,N-dimethylacrylamide solvate".

4. The compound of claim 1 "Stavudine N,N-dimethylpropionamide solvate".

5. A process for making Stavudine comprising breaking the precipitated solvate of a compound selected from the group of compounds in claim 1.

6. The process of claim 5 wherein the compound selected is the compound of claim 1(a).

7. The process of claim 5 wherein the compound selected is the compound of claim 1(b).

8. The process of claim 5 wherein the compound selected is the compound of claim 1(c).

9. A process for making any of the compounds of claim 1 which comprises reacting Stavudine with a compound selected from the group of compounds consisting of N,N-dimethylacetamide, N,N-dimethylacrylamide and N,N-dimethylpropionamide.

10. The process of claim 9 wherein Stavudine is reacted with N,N-dimethylacetamide.

11. The process of claim 9 wherein Stavudine is reacted with N,N-dimethylacrylamide.

12. The process of claim 9 wherein Stavudine is reacted with N,N-dimethylpropionamide.

13. The process of claim 5, 6, 7, or 8 wherein the solvates are broken by dissolving them in polar protic or aprotic solvents or combinations thereof at elevated temperatures in the range of 50–100° C., concentrating if necessary and then cooling to cause precipitation.

14. The process of claim 13 wherein the solvents are selected from the group consisting of water, alcohol, ketone and an amide other than those which form solvates.

15. The process of claim 14 wherein the ketone is selected from the group consisting of acetone, methyl ethyl ketone and methyl isobutyl ketone.

16. The process of claim 14 wherein the alcohol is selected from the group consisting of methanol, ethanol, 1-propanol, 2-propanol, 1-butanol and iso butanol.

17. Stavudine having a purity of at least 99.5% whenever made by the process of claim 5.

18. A pharmaceutical composition comprising Stavudine having a purity of at least 99.5% in a pharmaceutically acceptable carrier or diluent.

19. The process of claim 14 wherein the alcohol has 1–4 carbons.

20. The process of claim 9, 10, 11, or 12 further comprising the step of breaking the solvate so produced, to recover substantially pure Stavudine.

21. The process of claim 9, 10, 11, or 12 further comprising the step of breaking the solvate so produced, wherein the solvate is Stavudine N,N-dimethylacetamide solvate, to recover substantially pure Stavudine.

22. The process of claim 9, 10, 11, or 12 further comprising the step of breaking the solvate so produced, wherein the solvate is Stavudine N,N-dimethylacrylamide solvate, to recover substantially pure Stavudine.

23. The process of claim 9, 10, 11, or 12 further comprising the step of breaking the solvate so produced, wherein the solvate is Stavudine N,N-dimethylpropionamide solvate, to recover substantially pure Stavudine.

24. The process of claim 9, 10, 11 or 12 further comprising the step of breaking the precipitated solvate so produced, wherein the solvate is broken by dissolving said solvate in polar protic or aprotic solvents or combinations thereof at elevated temperatures in the range of 50–100° C., concentrating if necessary and then cooling to cause precipitation.

25. The process of claim 9, 10, 11 or 12 further comprising the step of breaking the solvate so produced, wherein the solvate Stavudine N,N-dimethylacetamide is broken by dissolving said solvate in polar protic or aprotic solvents or combinations thereof at elevated temperatures in the range of 50–100° C., concentrating if necessary and then cooling to cause precipitation.

26. The process of claim 9, 10, 11 or 12 further comprising the step of breaking the solvate so produced, wherein the solvate Stavudine N,N-dimethylacrylamide is broken by dissolving said solvate in polar protic or aprotic solvents or combinations thereof at elevated temperatures in the range of 50–100° C., concentrating if necessary and then cooling to cause precipitation.

27. The process of claim 9, 10, 11 or 12 further comprising the step of breaking the solvate so produced, wherein the solvate Stavudine N,N-dimethylpropionamide is broken by dissolving said solvate in polar protic or aprotic solvents or combinations thereof at elevated temperatures in the range of 50–100° C., concentrating if necessary and then cooling to cause precipitation.

28. The process of claim 24 wherein the solvents are selected from the group consisting air of water, alcohol, ketone and an amide other than those which form solvates wherein the ketone is selected from the group consisting of acetone, methyl ethyl ketone and methyl isobutyl ketone.

29. The process of claim 25 wherein the solvents are selected from the group consisting of water, alcohol, ketone and an amide other than those which form solvates wherein the ketone is selected from the group consisting of acetone, methyl ethyl ketone and methyl isobutyl ketone.

30. The process of claim 26 wherein the solvents are selected from the group consisting of water, alcohol, ketone and an amide other than those which form solvates wherein the ketone is selected from the group consisting of acetone, methyl ethyl ketone and methyl isobutyl ketone.

31. The process of claim 27 wherein the solvents are selected from the group consisting of water, alcohol, ketone and an amide other than those which form solvates wherein the ketone is selected from the group consisting of acetone, methyl ethyl ketone and methyl isobutyl ketone.

* * * * *